United States Patent [19]

Lin

[11] Patent Number: 5,360,430

[45] Date of Patent: Nov. 1, 1994

[54] INTERVERTEBRAL LOCKING DEVICE

[76] Inventor: Chih-I Lin, 513 S. Golden Pardos Dr., Diamond Bar, Calif. 10765

[21] Appl. No.: 98,855

[22] Filed: Jul. 29, 1993

[51] Int. Cl.⁵ ............................................. A61B 17/58
[52] U.S. Cl. ......................................... 606/61; 623/17
[58] Field of Search ........................ 606/61, 72; 623/17

[56] References Cited

U.S. PATENT DOCUMENTS

| | | | |
|---|---|---|---|
| 4,309,777 | 1/1982 | Patil | 606/61 |
| 4,932,975 | 6/1990 | Main et al. | 623/17 |
| 5,062,850 | 11/1991 | MacMillan et al. | 606/61 |
| 5,236,460 | 8/1993 | Barber | 606/61 |

FOREIGN PATENT DOCUMENTS 0317972 5/1989 European Pat. Off. ............... 623/17

Primary Examiner—Tamara L. Graysay
Attorney, Agent, or Firm—Bacon & Thomas

[57] ABSTRACT

An intervertebral locking device includes a bottom base, a bracing member, a top base, and at least one adjusting arm. The bottom base is provided on the upper surface thereof with a fastening member and on the lower surface thereof with one or more spikes. The bracing member has a bottom united with the fastening member attached to the upper surface of the bottom base. The top base is provided on the lower surface thereof with a fastening member and on the upper surface thereof with one or more spikes. The adjusting arm has one end serving as an adjusting end and another end acting as a locking end. The adjusting end of the adjusting arm is fastened to the bottom base or the top base in such a manner that the adjusting end is first adjusted to be in an appropriate position and is then fixed securely at that position. The locking end of the adjusting arm is fixed appropriately on one of the two vertebrae adjacent to a deformed or diseased vertebra under treatment.

3 Claims, 6 Drawing Sheets

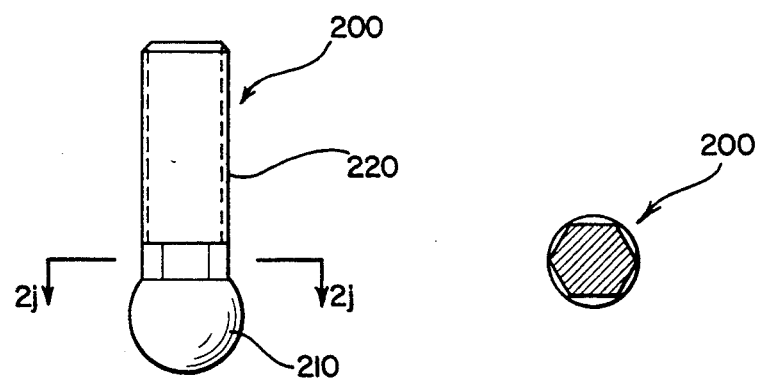
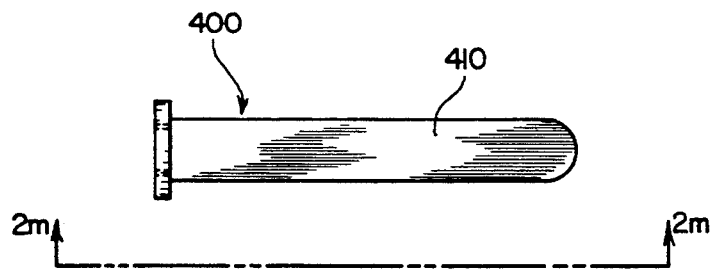
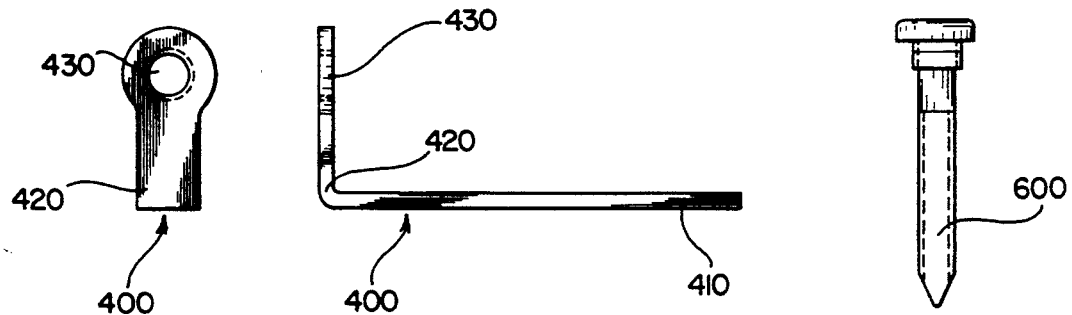

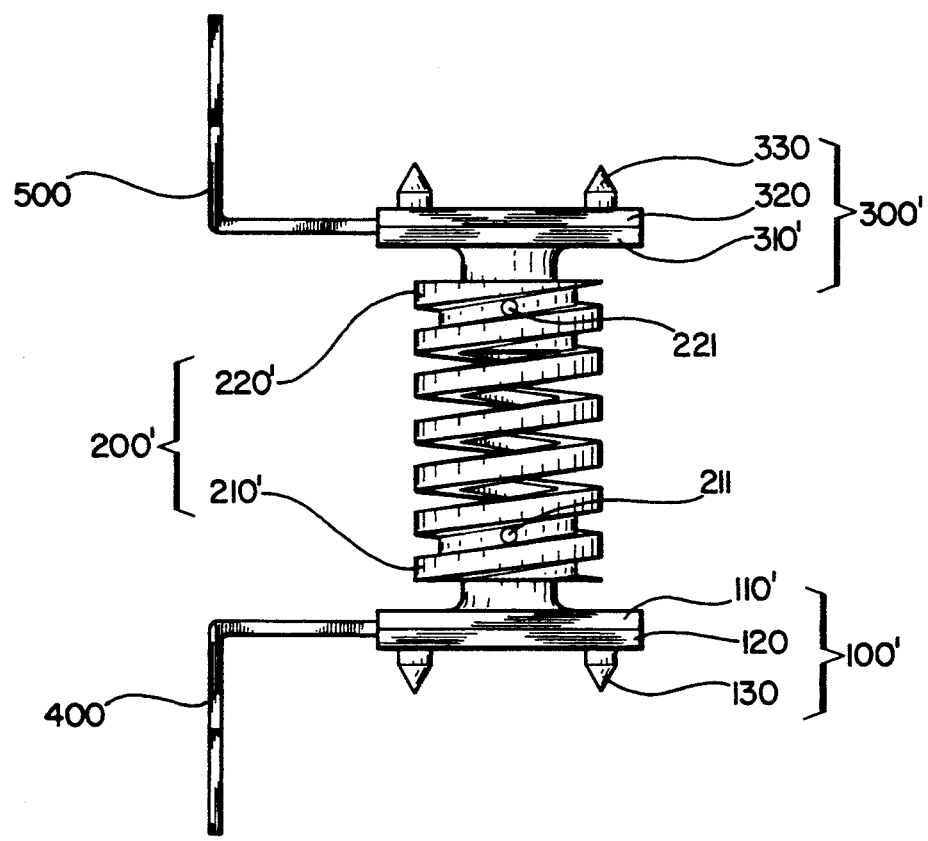
FIG. 3
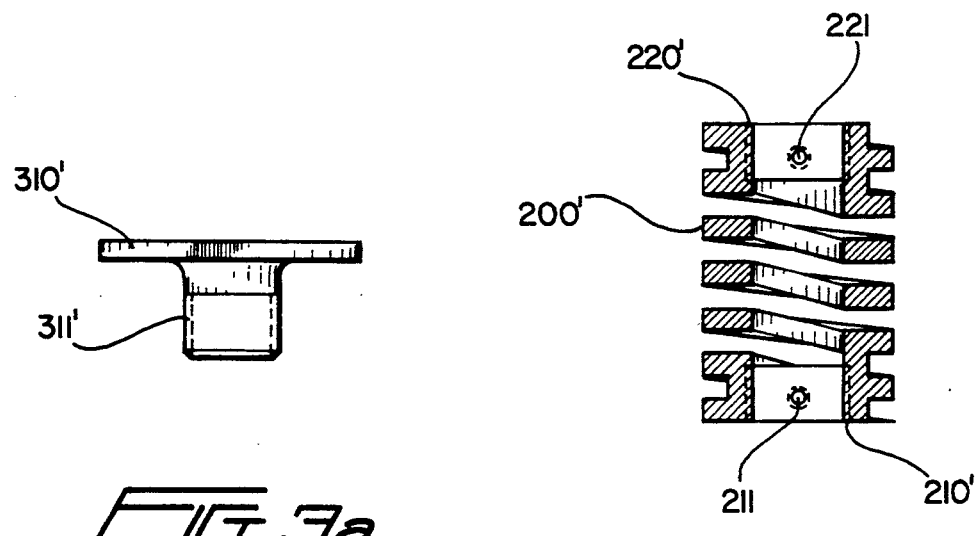
FIG. 3a
FIG. 3b

INTERVERTEBRAL LOCKING DEVICE

FIELD OF THE INVENTION

The invention relates generally to a spinal orthopedic device, and more particularly to an intervertebral locking device,

BACKGROUND OF THE INVENTION

The conventional intervertebral locking device, such as the BEZAIAN SPINAL FIXATOR made by Spinal and Orthopedic Devices, Inc. of the United States, is generally composed of a rigid structure which is capable of bracing two vertebrae adjacent to a deformed vertebra in such a manner that the two vertebrae are kept apart appropriately. The bracing of the two vertebbrae by the rigid structure is attained by means of a plurality of sharp-pointed projections located respectively at the upper and the lower ends of the rigid structure. In other words, the sharp-pointed projections of the rigid structure are made use of bearing almost entirely the pressure of a patient's body exerting on the vertebrae of the patient. However, the sharp-pointed projections of the implanted rigid structure are not exerted Upon uniformly by the pressure of the patient's body in view of the fact that the vertebrae of the human spinal column have different curvatures, thereby causing the implanted rigid structure to move in a specific direction. As a result, the implanted rigid structure can not be fixed securely on the axial wheel line of the vertebrae adjacent to the vertebra under treatment. In addition, the two vertebrae adjacent to the vertebra under treatmnet are so interfered with by the implanted rigid structure that they are not so located as to form therebetween an appropriate angle.

SUMMARY OF THE INVENTION

It is therefore the primary objective of the present invention to provide an intervertebral locking device with adjusting arms for use in adjusting and locking the upper and the lower ends of the intervertebral locking device, which are implanted respectively in the two vertebrae opposite to each other and adjacent to a deformed vertebra under treatment.

It is another objective of the present invention to provide an intervertebral locking device with a bracing member which is adjustable in a specified direction.

It is still another objective of the present invention to provide an intervertebral locking device made up of a bottom base, a bracing member, a top base, and adjusting arms.

In keeping with the principle of the present invention, the foregoing objectives of the present invention are accomplished by an intervertebral locking device comprising a bottom base, a bracing member, a top base and at least one adjusting arm. The bottom base is provided on the upper surface thereof with a fastening member and on the lower surface thereof with one or more protruded bodies or spikes. The bracing member has a bottom united with the fastening member attached to the upper surface of the bottom base. The top base is provided on the lower surface thereof with a fastening member and on the upper surface thereof with one or more protruded bodies or spikes. The adjusting arm has one end serving as an adjusting end and another end acting as a locking end. The adjusting end of the adjusting arm is fastened to the bottom base or the top base in such a manner that the adjusting end is first adjusted to be in an appropriate position and is then fixed securely at that position. The locking end of the adjusting arm is fixed appropriately on one of the two vertebrae adjacent to a deformed or diseased vertebra under treatment.

The foregoing objectives, features and functions of the present invention can be more fully understood by studying the following detailed description of the present invention in conjunction with the drawings provided herewith.

BRIEF DESCRIPTION OF THE DRAWINGS

FIG. 2a is an end view of a base plate incorporated in the intervertabral locking device of FIG. 1.

FIG. 2b is a cross-sectional view generally taken along line 2b–2b in FIG. 2a.

FIG. 2i is a schematic side view of a bracing member incorporated in the intervertebral locking device of FIG. 1.

FIG. 2j is a ross-sectional view generally taken along line 2j–2j of FIG. 2i.

FIG. 2k is an end view of an adjusting arm incorporated in the intervertebral locking device of the present invention.

FIG. 2i is an end view of the adjusting arm shown in FIG. 2k.

FIG. 2m is a side view of the adjusting arm generally taken along line 2m–2m of FIG. 2k.

FIG. 2n is a schematic side view of a locking screw incorporated in the intervertebral locking device of the invention.

FIG. 3 depicts a schematic view of a second preferred embodiment of the intervertebral locking device of the present invention.

FIG. 3a is a schematic side view of a top base incorporated in the intervertebral locking device of FIG. 3.

FIG. 3b is a cross-sectional view of a bracing member incorporated in the intervertebral locking device of FIG. 3.

DETAILED DESCRIPTION OF THE INVENTION

Figure 1:
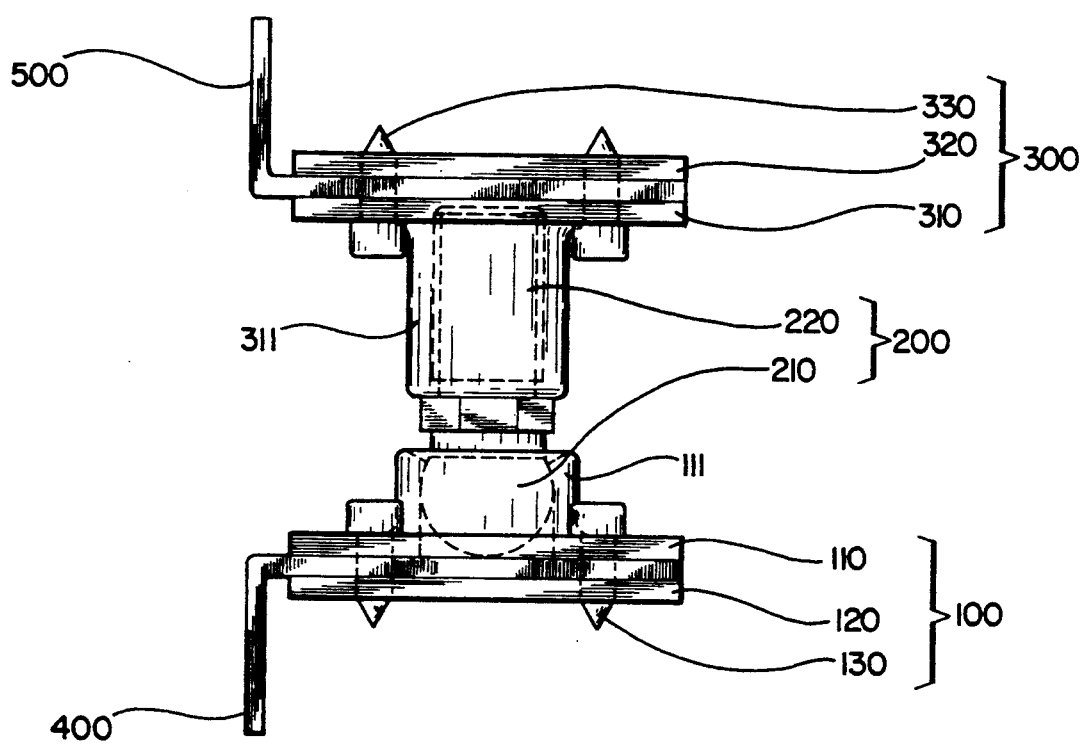
FIG. 1 shows a schematic side view of a preferred embodiment of the intervertebral locking device of the present invention.
Figures 2A, 2B:
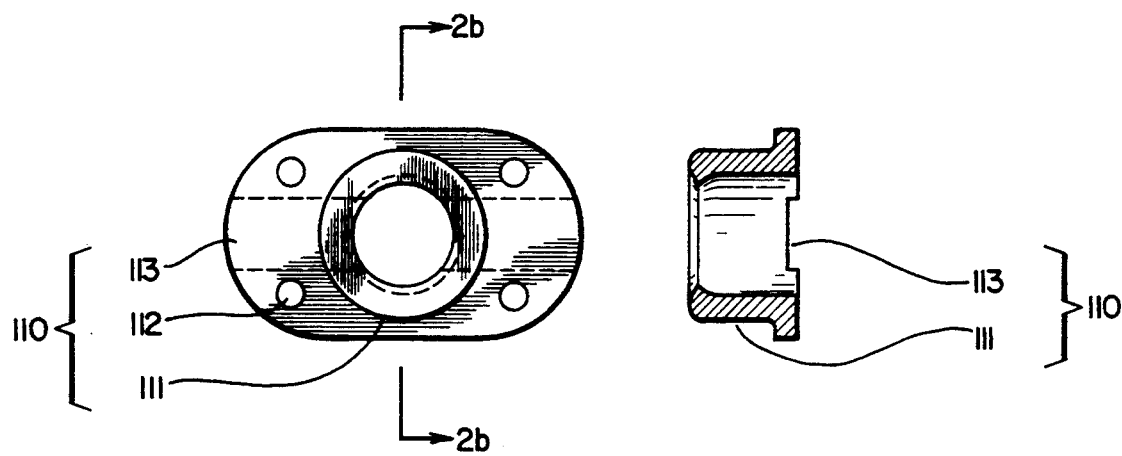
Figures 2C, 2D:
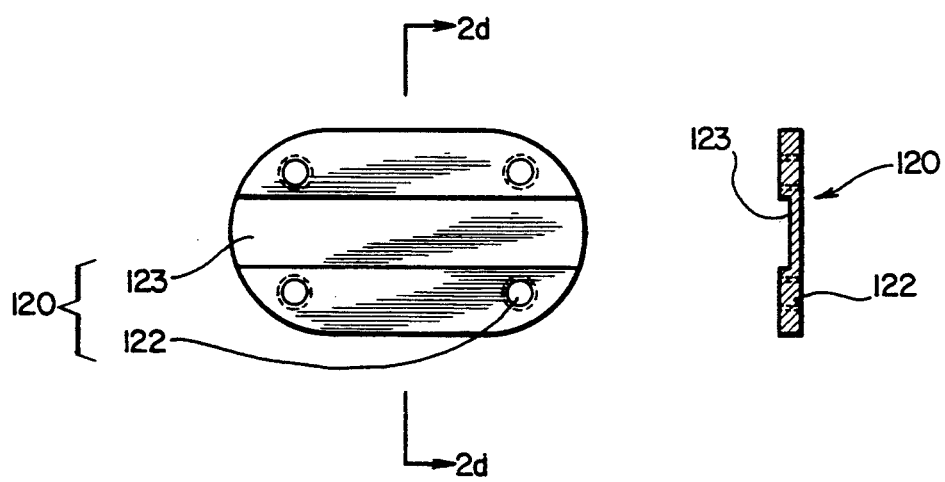
FIG. 2c is a top end view of a fastening plate incorporated in the intervertebral locking device of FIG. 1.
FIG. 2d is a cross-sectional view generally taken along line 2d–2d of FIG. 2c.

As shown in FIG. 1, an intervertebral locking device of a first preferred embodiment of the present invention comprises a bottom base 100, a bracing member 200, a top base 300, and two adjusting arms 400 and 500. The bottom base 100 is composed of a base plate 110, a fastening plate 120 and two screws 130. The base plate 110 is provided thereon with a fastening member 111 attached securely thereto. Each of the two screws 130 is fastened onto the bottom base 100 such that the screw 130 is put through a through hole of the base plate 110 so as to mesh with a threaded hole of the fastening plate 120, as shown respectively in FIGS. 2a and 2c, and that the sharp-pointed end of the screw 130 is allowed to penetrate the fastening plate 120 so as to emerge from the bottom surface of the fastening plate 120, as shown in FIG. 1. The bracing member 200 is provided with a lower end 210 of spherical construction and with an upper end 220 of cylindrical construction. The lower end 210 of the bracing member 200 is movably attached to the fastening member 111 of the bottom base 100, as shown in FIG. 1. The top base 300 is composed of a base plate 310, a fastening plate 320 and two screws 330. The base plate 310 of the bottom base 300 is provided on the lower surface thereof with a fastening member 311 which is united with the upper end 220 of the bracing member 200. The adjusting arm 400 is inserted into a slot located between the base plate 110 and the fastening plate 120, as shown in FIGS. 2b and 2d. The adjusting arm 500 is similarly disposed in a slot located between the base plate 310 and the fastening plate 320.

Figure 2E:
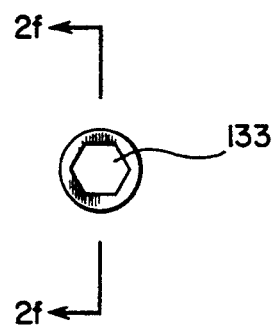
FIG. 2e is a top view of a screw utilized in the intervertebral locking device of FIG. 1.
Figure 2F:
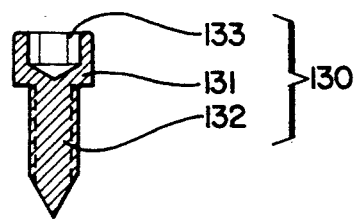
FIG. 2f is a cross-sectional view generally taken along line 2f–2f in FIG. 2e.
Figure 2G:
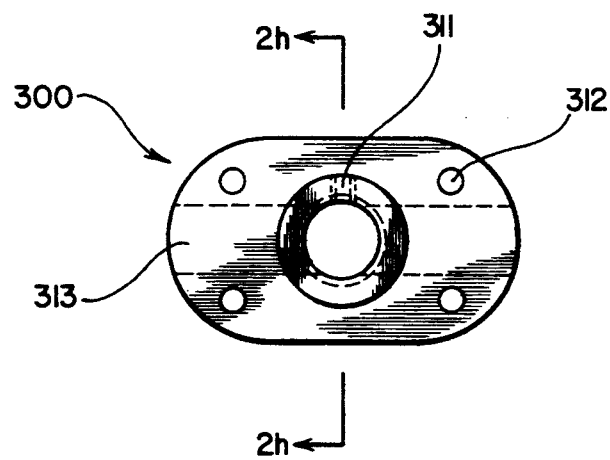
FIG. 2g is an end view of a top base incorporated in the intervertebral locking device of FIG. 1.
Figure 2H:
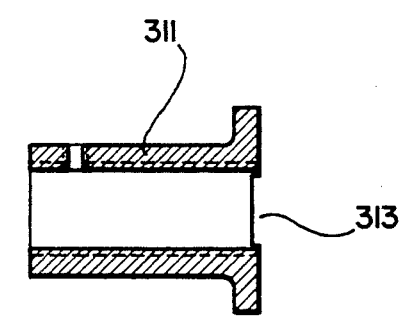
FIG. 2h is a cross-sectional view generally taken along line 2h–2h of FIG. 2g.

As shown in FIGS. 2a and 2b, the base plate 110 of the bottom base 100 is provided with a fastening member 111, through holes 112 and a centrally located slot 113. The fastening plate 120 of the bottom base 100 is shown in a top elevational view thereof and a sectional view thereof to comprise threaded holes 122 and a centrally located slot 123, as illustrated in FIGS. 2c and 2d. The top view and the sectional view of the screw 130 reveal that the screw 130 has a head 131, a protruded body or spike 132 and a tool hole 133, as illustrated in FIGS. 2e and 2f. If necessary, the screw 130 can be caused to fasten further securely onto the fastening plate 120 by means Of an expansion screw. The top view and the sectional view of the base plate 310 of the top base 300 reveal that the base plate 310 is composed of a fastening member 311, through holes 312 and a centrally located slot 313, as illustrated in FIGS. 2g and 2h. The side elevational view and the top view of the bracing member 200 show respectively that the upper end 220 of the bracing member 200 is well embraced by the fastening member 311 of the base plate 310, and that the lower end 210 is so dimensioned as to fit movably into the fastening member 111 of the base plate 110 of the bottom base 100, as illustrated in FIGS. 2i and 2j. The top view, the left elevational view and the side elevational view of the adjusting arm 400, as shown respectively in FIGS. 2k, 2l and 2m, reveal that the adjusting arm 400 is provided with an adjusting end 410, and a locking end 420 with a locking hole 430. A locking screw 600, as shown in FIG. 2n, is received in the locking hole 430 of the locking end 420 of the adjusting arm 400. Since adjusting arm 500 is constructed substantially identical to adjusting arm 400, no further description thereof will be provided.

A second preferred embodiment of the present invention is schematically shown in FIGS. 3, 3a and 3b. The second embodiment of the present invention is basically similar to the first preferred embodiment of the present invention, with the difference being that the second embodiment is provided with a bracing member 200' defining a spring body of an elastic material and having a serrated upper fastening portion 220' and a serrated lower fastening portion 210'. In other words, the bracing member 200' is fastened at both upper and lower ends thereof with the top base 300' and the bottom base 100 in such a manner that the serrated upper fastening portion 220' of the bracing member 200' engages a serrated fastening portion 311' of the base plate 310' of the top base 300', and that the serrated lower fastening portion 210' of the bracing member 200' engages a serrated fastening portion (not shown) of the base plate 110' of the bottom base 100', which is symmetrical to top base 300'. The bracing member 200' is fastened further securely with the serrated fastening portions by means of two screws (not shown) which are received and tightened respectively in two threaded holes 211 and 221 of the bracing member 200'.

It must be noted here that the phrase "upper end" used in the above description of the present invention refers to the end facing the neck portion of a patient's body in which the device of the present invention is implanted, and that the phrase "lower end" refers to the end opposite to the upper end.

Figure 4:
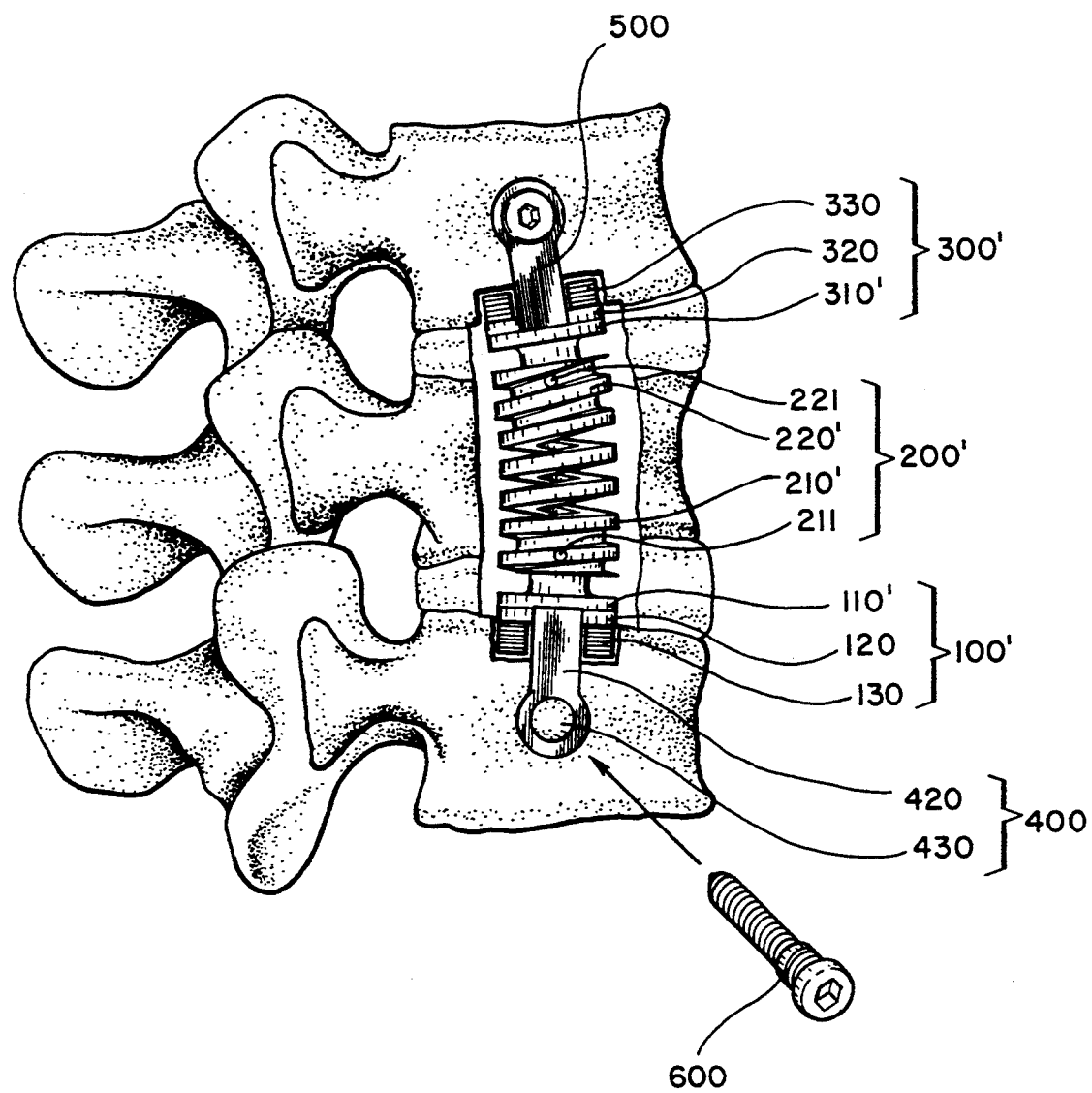
FIG. 4 is a perspective view depicting the intervertebral locking device of FIG. 3 implanted within a spinal column.

The implanted device of the second preferred embodiment of the present invention, as shown in FIGS. 3, 3a and 3b, is schematically illustrated in FIG. 4. The device of the present invention is securely implanted in the vertebrae by means of locking screw 600 engaging a threaded hole 430.

The device of the present invention described above is made of a biocompatible material suitable for the orthopedic surgery, such as stainless steel 316 LVM, or the titanium-based material like Ti-6-4, or the cobalt-molybdenum-nickel alloy, etc.

The bottom base 100, 100' of the device of the present invention may be of a singular type or a plural type, preferably the latter. The bottom base of the singular type comprises an upper planar surface, a lower planar surface, and a single base plate. The upper planar surface is provided with a fastening member. The lower planar surface has a protruded body. The single base plate is provided centrally with a slide groove for accommodating the adjusting arm 400. The bottom base of the plural type is composed of a base plate with a plurality of through holes, a fastening plate provided centrally with a slot and a plurality of threaded holes corresponding in number and location to the through holes, and a plurality of screws. The method of fastening the bottom base of the plural type includes the steps of: (a) arranging the fastening plate such that the centrally located slot faces upwards and that the thread holes are aligned with the through holes; (b) putting the screws into the through holes of the base plate; (c) engaging the screws with the threaded holes of the fastening plate, without tightening the screws; (d) inserting the adjusting arm into the slot before tightening the screws; and (e) locating securely the adjusting arm between the base plate and the fastening plate by tightening the screws. It must be noted here that the portion of each of the screws which penetrates beyond the fastening plate constitutes the protruded body. The fastening member attached to the upper planar surface of the bottom base is a conventional fastener, such as a nut for fastening the upper end of the bracing member 200, 200' or a receiving mount of annular construction for receiving the lower end of the bracing member 200, 200'.

Similarly, the top base 300, 300' of the device of the present invention may be of a singular type or a plural type, preferably the latter. However, the bottom base 100, 100' and the top base 300, 300' are not necessarily identical with each other in construction.

The bracing member 200, 200' of the device of the present invention may be of any shape or dimension, depending on the position of the vertebra intended to be fixed and on the constructions of the fastening members of the bottom base 100, 100' and the top base 300, 300'. For example, if the fastening members of the bottom base 100, 100' and the top base 300, 300' are of nut-shaped construction, the bracing member 200, 200' should be provided respectively at both upper and lower ends thereof with a threaded mount engageable with the nut-shaped fastening member of the bottom base 100, 100' or the top base 300, 300'. The bracing member 200, 200' of elastic material is capable of making an angle adjustment by itself. On the other hand, if the fastening members of the bottom base 100, 100' and the top base 300, 300' are of ring-shaped projection, the bracing member 200, 200' should be provided respectively at both upper and lower ends thereof with a cylindrical body engageable with the ring-shaped fastening member of the bottom base 100, 100' or the top base 300, 300'. The bracing member 200 should have at least one end of spherical construction so as to enable the bracing member 200, 200' to adjust the angle at which the bracing member 200, 200' is fastened with the fastening member of the bottom base 100, 100' or the top base 300, 300'.

The embodiments of the present invention described above are to be regarded in all respects as merely illustrative and not restrictive. Accordingly, the present invention may be embodied in other specific forms without deviating from the spirit thereof. The present invention is therefore to be limited only by the scope of the following appended claims.

I claim:

1. An intervertebral locking device comprising:
   a bottom base having an upper planar surface with a fastening member attached thereto and having a lower planar surface with one or more protruded bodies;
   a bracing member having a lower end united with said fastening member attached to said upper planar surface of said bottom base and an upper end;
   a top base having a lower planar surface with a fastening member attached thereto which, in turn, is attached to the upper end of said bracing member, and having an upper planar surface with one or more protruded bodies; and
   a pair of adjusting arms each having one end serving as an adjusting end to fasten adjustably with said bottom base and said top base respectively, each of said adjusting arms further having another end acting as a locking end to anchor securely in an appropriate position with one of said locking ends being adapted to be secured to a vertebra adjacent to a deformed vertebra under treatment;
   wherein said adjusting ends of said adjusting arms are securely fastened with said bottom base and said top base respectively after said adjusting ends are first adjusted to locate appropriately said locking ends;
   wherein said bottom base and said top base are provided respectively with a base plate having a plurality of through holes, a fastening plate having a plurality of threaded holes corresponding in number and location to said through holes, and a plurality of screws which are put through said through holes of said base plate to engage said threaded holes of said fastening plate in such a manner that said screws penetrate said fastening plate to form a plurality of said protruded bodies; and
   wherein said adjusting end of each of said adjusting arms is received in a slot centrally locate between said bottom base and said fastening plate.

2. An intervertebral locking device comprising:
   a bottom base having an upper planar surface with a fastening member attached thereto and having a lower planar surface with one or more protruded bodies;
   a bracing member having a lower end united with said fastening member attached to said upper planar surface of said bottom base and an upper end;
   a top base having a lower planar surface with a fastening member attached thereto which, in turn, is attached to the upper end of said bracing member, and having an upper planar surface with one or more protruded bodies; and
   a pair of adjusting arms each having one end serving as an adjusting end to fasten adjustably with said bottom base and said top base respectively, each of said adjusting arms further having another end acting as a locking end to anchor securely in an appropriate position with one of said locking ends being adapted to be secured to a vertebra adjacent to a deformed vertebra under treatment;
   wherein said adjusting ends of said adjusting arms are securely fastened with said bottom base and said top base respectively after said adjusting ends are first adjusted to locate appropriately said locking ends; and
   wherein said bracing member is a spring body and is fastened with said top base and said bottom base by means of two serrated fastening members located respectively at the upper end and the lower end of said bracing member, with said two serrated fastening members of said bracing member engaging respectively said fastening member of said top base and said fastening member of said bottom base.

3. An intervertebral locking device comprising:
   a bottom base having an upper planar surface with a fastening member attached thereto and having a lower planar surface with one or more protruded bodies;
   a bracing member having a lower end united with said fastening member attached to said upper planar surface of said bottom base and an upper end;
   a top base having a lower planar surface with a fastening member attached thereto which, in turn, is attached to the upper end of said bracing member, and having an upper planar surface with one or more protruded bodies; and
   a pair of adjusting arms each having one end serving as an adjusting end to fasten adjustably with said bottom base and said top base respectively, each of said adjusting arms further having another end acting as a locking end to anchor securely in an appropriate position with one of said locking ends being adapted to be secured to a vertebra adjacent to a deformed vertebra under treatment;
   wherein said adjusting ends of said adjusting arms are securely fastened with said bottom base and said top base respectively after said adjusting ends are first adjusted to locate appropriately said locking ends; and
   wherein said bracing member has at least one end of spherical construction and so dimensioned as to fasten with a receiving mount of ring-shaped construction of said fastening member of said bottom base.

* * * * *